(12) United States Patent
Anderson

(10) Patent No.: US 8,249,689 B2
(45) Date of Patent: Aug. 21, 2012

(54) COIL ARRANGEMENT FOR ELECTROMAGNETIC TRACKING METHOD AND SYSTEM

(75) Inventor: Peter Traneus Anderson, Andover, MA (US)

(73) Assignee: General Electric Company, Schenectady, NY (US)

( * ) Notice: Subject to any disclaimer, the term of this patent is extended or adjusted under 35 U.S.C. 154(b) by 1581 days.

(21) Appl. No.: 11/710,085

(22) Filed: Feb. 23, 2007

(65) Prior Publication Data

US 2008/0204004 A1 Aug. 28, 2008

(51) Int. Cl.
*A61B 5/05* (2006.01)

(52) U.S. Cl. ........................................ 600/424

(58) Field of Classification Search .................. 600/424; 336/198
See application file for complete search history.

(56) References Cited

U.S. PATENT DOCUMENTS

| | | |
|---|---|---|
| 1,450,080 A | 3/1923 | Hazeltine |
| 4,710,708 A | 12/1987 | Rorden |
| 4,849,692 A | 7/1989 | Blood |
| 4,945,305 A | 7/1990 | Blood |
| 5,425,382 A | 6/1995 | Golden |
| 5,558,091 A | 9/1996 | Acker |
| 5,592,939 A | 1/1997 | Martinelli |
| 5,640,170 A | 6/1997 | Anderson |
| 5,676,673 A | 10/1997 | Ferre |
| 5,747,996 A | 5/1998 | Fuchs |
| 5,782,765 A | 7/1998 | Jonkman |
| 5,800,352 A | 9/1998 | Ferre |
| 5,803,089 A | 9/1998 | Ferre |
| 5,829,444 A | 11/1998 | Ferre |
| 5,873,822 A | 2/1999 | Ferre |
| 5,879,297 A | 3/1999 | Haynor et al. |
| 5,913,820 A | 6/1999 | Bladen |
| 5,967,980 A | 10/1999 | Ferre |
| 6,052,610 A | 4/2000 | Koch |
| 6,073,043 A | 6/2000 | Schneider |
| 6,129,668 A | 10/2000 | Haynor |
| 6,172,499 B1 | 1/2001 | Ashe |
| 6,175,756 B1 | 1/2001 | Ferre |
| 6,201,387 B1 | 3/2001 | Govari |
| 6,226,547 B1 | 5/2001 | Lockhart |
| 6,246,231 B1 | 6/2001 | Ashe |
| 6,374,134 B1 | 4/2002 | Bladen |
| 6,445,943 B1 | 9/2002 | Ferre |
| 6,502,031 B2 | 12/2002 | Uehara |

(Continued)

FOREIGN PATENT DOCUMENTS

WO WO9736192 10/1997

OTHER PUBLICATIONS

Takaaki Nara, et al.; "A Closed-Form Formula for Magnetic Dipole Localization by Measurement of its Magnetic Field and Spatial Gradients"; Digital Object Identifier; 2006 IEEE; pp. 3291-3293.

(Continued)

*Primary Examiner* — Brian Casler
*Assistant Examiner* — Saurel J Selkin
(74) *Attorney, Agent, or Firm* — Fletcher Yoder, PC

(57) ABSTRACT

An electromagnetic tracking coil arrangement, comprising three co-planar electromagnetic sensors and a fourth electromagnetic sensor that is not co-planar with the three co-planar sensors, wherein the three co-planar electromagnetic sensors and the fourth electromagnetic sensor are each located at a vertex of a tetrahedron.

10 Claims, 5 Drawing Sheets

U.S. PATENT DOCUMENTS

| | | |
|---|---|---|
| 6,539,327 B1 | 3/2003 | Dassot |
| 6,701,179 B1 | 3/2004 | Martinelli |
| 6,774,624 B2 | 8/2004 | Anderson |
| 6,980,921 B2 | 12/2005 | Anderson |
| 7,015,859 B2 | 3/2006 | Anderson |
| 7,096,148 B2 | 8/2006 | Anderson |
| 7,158,754 B2 | 1/2007 | Anderson |
| 2002/0026127 A1* | 2/2002 | Balbierz et al. ............... 600/567 |
| 2003/0088179 A1 | 5/2003 | Seeley et al. |
| 2004/0186681 A1 | 9/2004 | Harle |
| 2005/0065433 A1* | 3/2005 | Anderson ..................... 600/424 |
| 2005/0146327 A1* | 7/2005 | Jakab ........................... 324/302 |
| 2006/0058604 A1 | 3/2006 | Avinash |
| 2006/0106292 A1 | 5/2006 | Anderson |
| 2006/0247511 A1 | 11/2006 | Anderson |
| 2008/0154120 A1* | 6/2008 | von Jako et al. .............. 600/411 |
| 2008/0177177 A1* | 7/2008 | Aoki et al. .................... 600/424 |

OTHER PUBLICATIONS

"4—Sensor Gradiometer (GSM-19GW4 v7.0)" GEM Systems, Inc. Advanced Magnetometers.

Office Action from corresponding CN Application No. 200810081457.4, Oct. 11, 2010.

* cited by examiner

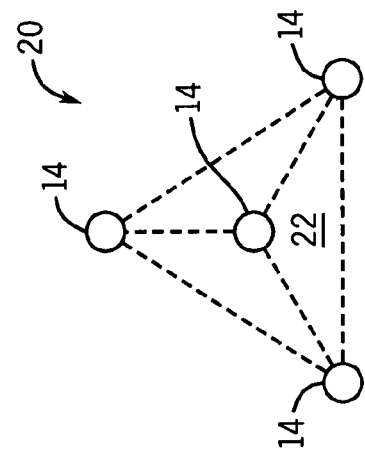
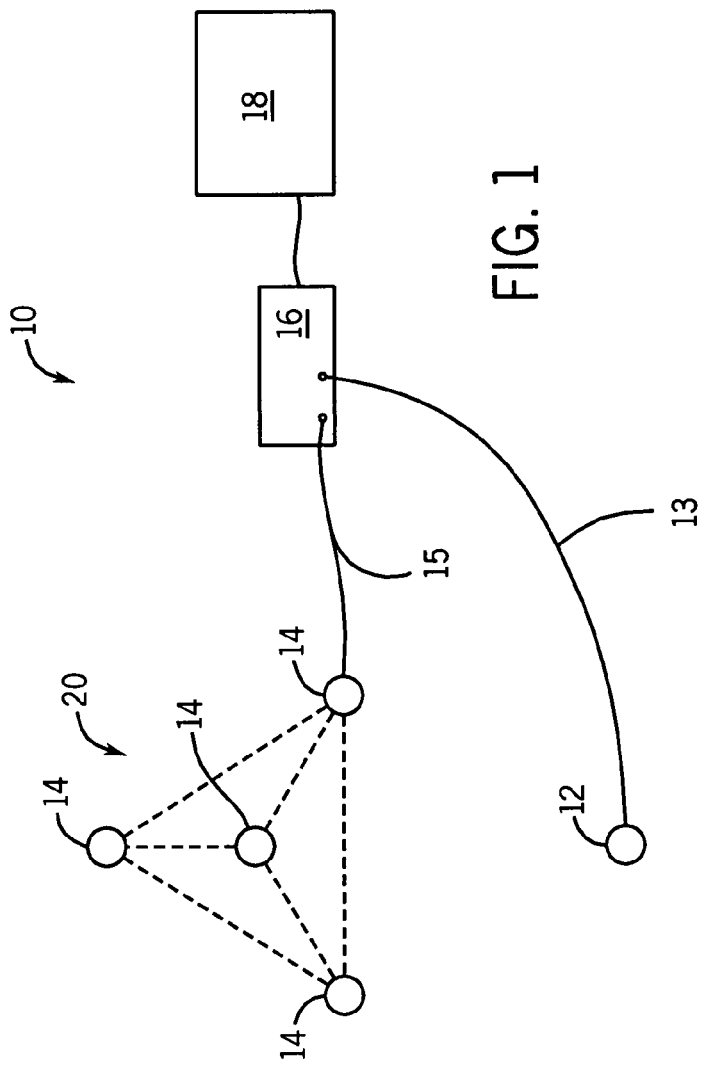
FIG. 1
FIG. 2

COIL ARRANGEMENT FOR ELECTROMAGNETIC TRACKING METHOD AND SYSTEM

BACKGROUND

This disclosure relates generally to tracking systems that use magnetic fields to determine the position and orientation of an object, such as systems used for tracking instruments and devices during surgical interventions and other medical procedures. More particularly, this disclosure relates to a system and method for electromagnetic tracking that utilizes a compact coil arrangement.

Tracking systems have been used in various industries and applications to provide position information relating to objects. For example, electromagnetic tracking may be useful in aviation applications, motion sensing applications, and medical applications. In medical applications, tracking systems have been used to provide an operator (e.g., a physician) with information to assist in the precise and rapid positioning of a medical device located in or near a patient's body. In general, an image may be displayed on a monitor to provide positioning information to an operator. The image may include a visualization of the patient's anatomy with an icon on the image representing the device. As the device is positioned with respect to the patient's body, the displayed image is updated to reflect the correct device coordinates. The base image of the patient's anatomy may be generated either prior to or during the medical procedure. For example, any suitable medical imaging technique, such as X-ray, computed tomography (CT), magnetic resonance imaging (MRI), positron emission tomography (PET), and ultrasound, may be utilized to provide the base image displayed during tracking. The combination of the base image and the representation of the tracked device provides positioning information that allows a medical practitioner to manipulate a device to a desired position and/or associate information gathered to a precise location.

To determine device location, tracking systems may utilize a method of electromagnetic (EM) field generation and detection. Using this method, at least one magnetic field is generated from one or more EM sensors (e.g., EM field generators or transmitters), and the magnetic fields are detected by one or more complementary EM sensors (e.g., EM receivers). In such a system the EM field may be detected by measuring the mutual inductance between the EM sensors and the complementary EM sensors. The measured values are processed to resolve a position and/or orientation of the EM sensors relative to one another. For example, an electromagnetic tracking system may include an EM sensor mounted at the operative end of a device and a complementary EM sensor fixed in a known position. When the EM sensor generates a magnetic field, a voltage indicative of the mutual inductance may be induced across the complementary EM sensor. The signal may be sensed and transmitted to a processor for processing. Processing may then use the measured voltage signal indicative of mutual inductance to determine the position and orientation of the EM sensors relative to one another (e.g., the X, Y and Z coordinates, as well as the roll, pitch and yaw angles).

Generally electromagnetic tracking systems contain EM sensors that consist of an array of one or more EM field generators and an array of or more EM receivers. To provide for more accurate device tracking, various arrangements of EM sensors around a tracking area have been used. For example, four EM sensors may be located at the corners of a rectangular region. In this configuration, a single EM sensor may act as act as an EM field generator generating magnetic fields that are sensed by the complementary EM sensor acting as an EM receiver. A processor may then receive the signals indicative of the detected magnetic fields and triangulate the position and/or orientation of the EM sensors.

Although the previously described methods may provide sufficient accuracy, there are several instances in which the sensors located about the periphery of a region in a single plane do not provide a sufficient estimate of position and/or orientation. For example, when four EM receivers are located in a single plane (e.g., on top of a surgery table) processing may be unable to accurately track the distance of an EM field generator above or below the plane. Further, even if the distance is determined, it may be difficult (if not impossible) for processing to determine on which side of the plane the EM field generator is located. For example, the same mutual inductance measurements may be present for an EM field generator located above the plane at a given position (x, y, z) and an EM field generator located below the plane at a given position (x, y, −z). This is because at both locations the EM field generator is the same distance from the EM receivers and, therefore, the mutual inductance measurements and their ratios used for triangulation are the same. Thus, processing is unable to resolve on which side of the plane the EM field generator is located.

In addition, some tracking system applications require compact EM sensors. Some EM sensors that contain a number of coils can be quite large. Industry standard coil architecture (ISCA) EM sensor assemblies are advantageous for these applications because they are small. However, the ISCA transmitter and receiver each comprise three approximately concentric and approximately orthogonal coils. Also, the ISCA coils must be individually characterized. When an ISCA transmitter or receiver needs to be mounted in the tip of a surgical instrument, space is restricted, making the use of a three coil device difficult.

Accordingly, there is a desire to provide an EM tracking system, wherein the EM sensors include at least one compact coil array.

BRIEF DESCRIPTION

In accordance with an aspect, provided is an electromagnetic coil arrangement, comprising three co-planar electromagnetic sensors and a fourth electromagnetic sensor that is not co-planar with the three co-planar sensors, wherein the three co-planar electromagnetic sensors and the fourth electromagnetic sensor are each located at a vertex of a tetrahedron.

In accordance with another aspect, provided is an electromagnetic tracking system, comprising an electromagnetic sensor arrangement comprising three co-planar electromagnetic sensors and a fourth electromagnetic sensor that is not co-planar with the three co-planar sensors, wherein the three co-planar electromagnetic sensors and the fourth electromagnetic sensor are each located at a vertex of a tetrahedron, and at least one complementary electromagnetic sensor.

In accordance with yet another aspect, provided is a method of electromagnetic tracking comprising providing at least one electromagnetic field generator for generating at least one magnetic field, providing an array of electromagnetic receivers for sensing at least one characteristic of the at least one magnetic field, wherein the array of electromagnetic receivers comprises three co-planar electromagnetic receivers and a fourth electromagnetic receiver that is not co-planar with the three co-planar receivers, and wherein the three co-planar electromagnetic receivers and the fourth electromagnetic receiver are each located at a vertex of a tetrahedron, and transmitting at least one signal indicative of the at least one characteristic of the at least one magnetic field to a processor.

In accordance with still yet another aspect, provided is an electromagnetic coil arrangement, comprising a plurality of electromagnetic sensors arranged around a volumetric region, wherein each of the plurality of electromagnetic sensors are spaced apart from each other, and wherein the plurality of electromagnetic sensors are not all in the same plane.

DRAWINGS

These and other features, aspects, and advantages of the present invention will become better understood when the following detailed description is read with reference to the accompanying drawings in which like characters represent like parts throughout the drawings, wherein:

FIG. 1 is an illustration of an exemplary system for EM tracking implementing certain aspects of the present technique;

FIG. 2 is an illustration of an exemplary sensor arrangement in accordance with certain aspects of the present technique;

DETAILED DESCRIPTION

Figure 4:
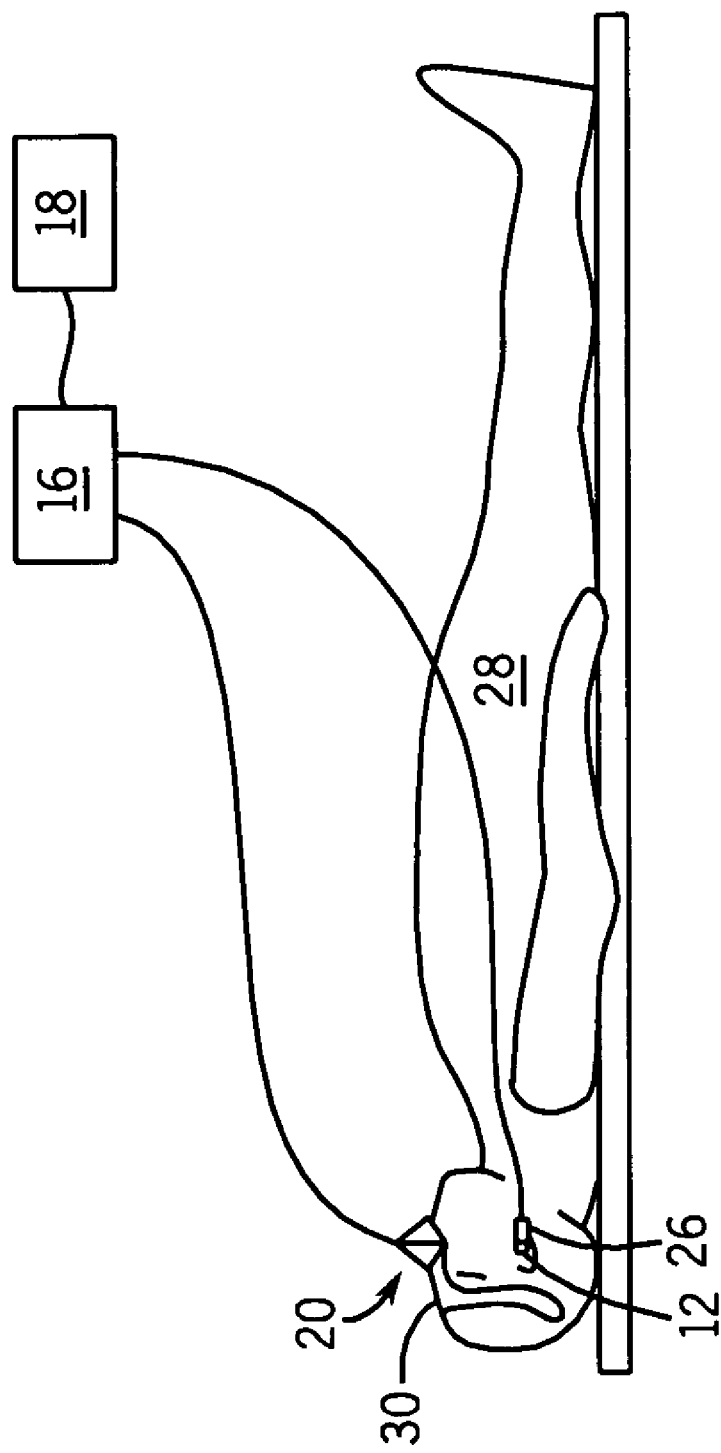
FIG. 4 is an illustration of the exemplary sensor arrangement of FIG. 2 disposed about a patient in accordance with certain aspects of the present technique.

Referring now to FIG. 1, a tracking system 10 in accordance with an embodiment of the present technique is illustrated. The tracking system 10 may generally include multiple tracking components. As depicted, the tracking components may include an electromagnetic (EM) coil arrangement 20 with a plurality of EM sensors 14, at least one complementary EM sensor 12, a processor 16 and a user interface 18. The at least one complementary EM sensor 12 may be coupled to at least one instrument or device 26, as shown in FIG. 4.

In the illustrated embodiment, the EM coil arrangement 20 comprises an array of EM sensors 14 arranged around a volumetric region 22. The array of EM sensors 14 may be formed from magnetic dipoles (e.g., coils, current loops, or electromagnets) capable of producing a dipole magnetic field when a current is applied or induced across them. In some embodiments, the EM sensors 14 may employ industry-standard coil architecture (ISCA) type coils, a single dipole coil, a planar coil, or a combination of the three. ISCA type coils are defined as three approximately collocated, approximately orthogonal, and approximately dipole coils. The array of EM sensors 14 may be configured with multiple coils capable of providing multiple dipole magnetic fields of varying magnitude and direction. By way of example, the array of EM sensors 14 may be implemented wherein each of the EM sensors 14 includes three concentric and orthogonal dipole coils (coil trios) and thus generates a dipole magnetic field in three planes (i.e., x, y and z planes).

Similarly, the at least one complementary EM sensor 12 may be formed from magnetic dipoles (e.g., coils, current loops, or electromagnets) capable of producing a dipole magnetic field when a current is applied or induced across them. In some embodiments, the at least one complementary EM sensor 12 may employ industry-standard coil architecture (ISCA) type coils, a single dipole coil, a planar coil, or a combination of the three. ISCA type coils are defined as three approximately collocated, approximately orthogonal, and approximately dipole coils. The at least one complementary EM sensor 12 may be configured with a single coil that generates a single dipole magnetic field.

The at least one complementary EM sensor 12 may be configured as an EM field generator or transmitter to generate a magnetic field, and the array of EM sensors 14 may be configured as an array of EM receivers to sense the magnetic field generated by the at least one complementary EM sensor 12.

The magnetic field generated by the at least one complementary EM sensor 12 may be dependent upon a current that is provided through the coil of the at least one complementary EM sensor 12. In an embodiment, to provide a current through the coil, the processor 16 may provide a drive current to the at least one complementary EM sensor 12, via a cable 13, as illustrated in FIG. 1. As will be appreciated, the at least one complementary EM sensor 12 may also operate in a wireless configuration that does not require a cable connection between the at least one complementary EM sensor 12 and processor 16. With the current flowing through the coil of the at least one complementary EM sensor 12, the at least one complementary EM sensor 12 may generate at least one dipole magnetic field with a given magnitude and direction. Characteristics of the magnetic field (e.g., magnitude, direction, phase or frequency) may be varied by manipulating the current.

The generated magnetic field may induce a current across the coils of the array of EM sensors 14. The array of EM sensors 14 sense the magnetic field, and transmit data to the processor 16. The data gathered by the array of EM sensors 14 may be processed to determine various parameters. For example, in the illustrated embodiment of FIG. 1, the magnetic field sensed by the array of EM sensors 14 may be output to processor 16, via a cable 15. As will be appreciated, the array of EM sensors 14 may also operate in a wireless configuration that does not require a cable connection between the array of EM sensors 14 and processor 16. The processor 16 may distinguish various magnetic fields by identifying the respective phase and frequency. As will be appreciated, depending on the number of magnetic fields generated and received, multiple degrees of freedom may be resolved by the processor 16. For example, wherein the array of EM sensors 14 and the at least one complementary EM sensor 12 each include a coil trio, six degrees of freedom, including three position values and three orientation values may be determined (i.e., x, y, z and roll, pitch, yaw).

In the tracking system 10, the at least one complimentary EM sensor 12 may include at least one conductive coil that generates an electromagnetic field when a current is passed through the coil. In certain embodiments, the at least one complimentary EM sensor 12 may include a single dipole coil. When a current is applied or induced across a single dipole coil a single magnetic field may be generated with a magnitude moment vector along its "axis." For a coil the direction of the coil axis is perpendicular to the plane of the coil in accordance with the right-hand rule. Those of ordinary skill in the art will appreciate that multiple transmitting coils may be used in coordination to generate multiple magnetic fields. For example, the at least one complimentary EM sensor 12 may be formed from three collocated orthogonal quasidipole coils (i.e., a coil trio). When a coil trio is energized, each coil may generate a magnetic field. As a result, three magnetic fields may be generated with magnitude vectors that are collocated and orthogonal to one another.

The array of EM sensors 14 are configured to "receive" (i.e., sense) the magnetic field(s) generated by the at least one EM sensor 12. For example, when a current is applied to the at least one EM sensor 12, the magnetic field generated by a coil of the at least one EM sensor 12 may induce a voltage into a coil of the array of EM sensors 14. The induced voltage may be indicative of the mutual inductance between the coil of the at least one EM sensor 12 generating the magnetic field and the coil of the array of EM sensors 14 sensing the magnetic field. Thus, the induced voltage across the coil of the array of EM sensors 14 may be sensed and processed to determine the mutual inductance between a coil of the at least one EM sensor 12 and a coil of the array of EM sensors 14.

The position and functionality of the at least one complementary EM sensor 12 with respect to the array of EM sensors 14 in the system 10 may be reversed. For example, in an embodiment, the at least one complementary EM sensor 12 may be configured as an EM receiver to sense a magnetic field, while the EM sensors 14 may be configured as EM field generators or transmitters to generate a magnetic field. However, for simplicity, the remainder of this discussion may refer to the at least one EM sensor 12 as an EM field generator or transmitter generating a magnetic field and the EM sensors 14 as EM receivers sensing a magnetic field.

Similar to the at least one EM sensor 12, the array of EM sensors 14 may employ a single dipole coil or multiple coils (e.g., a coil trio). For example, tracking systems may include an industry-standard coil architecture (ISCA) type coils. ISCA type coils are configured with at least one three-axis dipole coil transmitter and at least one three-axis dipole coil receiver. ISCA type coils are defined as three approximately collocated, approximately orthogonal, and approximately dipole coils. In such a configuration, the coils of the at least one EM sensor 12 and the coils of the array of EM sensors 14 are configured such that the three coils exhibit the same effective area, are oriented orthogonally one another, and are centered at the same point. Using this configuration, nine parameter measurements may be obtained (i.e., a measurement between each transmitting coil and each receiving coil). From the nine parameter measurements, processing may determine position and orientation information for each coil of the at least one EM sensor 12 with respect to each coil of the array of EM sensors 14. If either of the at least one EM sensor 14 or array of EM sensors 12 is in a known position, processing may also resolve position and orientation relative to the known position.

Further, the array of EM sensors 14 may include configurations other than a coil. For example, the array of EM sensors 14 may employ other technologies including Hall Effect, magnetoresistance and flux gate devices. For simplicity, the remainder of this discussion centers on the use of coils in the at least one EM sensors 12 and coils in the array of EM sensors 14.

As mentioned previously, the magnetic field generated requires a current be driven through a coil of the at least one EM sensor 12. In an embodiment, the processor 16 may provide a drive current to energize the coil(s) of at least one EM sensor 12 and, thereby, generate the magnetic field(s) that are sensed by the array of EM sensors 14. For example, the processor 16 may transmit a drive current to the at least one EM sensor 12 via a cabled connection. As will be appreciated, the source of the drive current may also be independent from the processor 16. For example, in another embodiment the at least one EM sensor 12 may include an oscillator that generates the drive current configured to produce a magnetic field. As will be appreciated, in tracking embodiments including the use of multiple generating coils in the at least one EM sensor 12, the drive current may include waveforms of varying phase and frequency to generate magnetic fields of varying phase and frequency that may be distinguished in processing.

In addition to providing a drive current, the processor 16 may process the received signals to track the position and orientation of an instrument or device. For example, array of EM sensors 14 will produce output signals that are proportional to the mutual inductance between at least one EM sensor 12 and the array of EM sensors 14. The processor 16 may use may use ratios of the mutual inductance measurements to triangulate the position of at least one EM sensor 12 relative to the array of EM sensors 14.

In general, the processor 16 may perform several functions in the tracking system 10. For example, the processor 16 may include electronic circuitry to provide the drive signals, electronic circuitry to receive the sensed signals, and electronic circuitry to condition the drive signals and the sensed signals. Further, the processor 16 may include processing to coordinate functions of the system 10, to implement navigation and visualization algorithms suitable for tracking and displaying the position and orientation of an instrument or device on a monitor. The processor 16 may include a digital signal processor, memory, a central processing unit (CPU) or the like, for processing the acquired signals. As will be appreciated, the processing may include the use of one or more computers within the processor 16. The addition of a separate CPU may provide additional functions for tracking, including, but not limited to, signal processing of data received, and transmission of data to the user interface 18, including a display. In an embodiment, the CPU may be confined within the processor 16, while in another embodiment a CPU may include a stand-alone device that is separate from the processor 16.

As mentioned, system 10 may also include a user interface 18. For example, the system 10 may include a monitor to display the determined position and orientation of a tracked object. As will be appreciated, the user interface 18 may include additional devices to facilitate the exchange of data between the system 10 and the user. For example, the user interface 18 may include a keyboard, mouse, printers or other peripherals. While the processor 16 and the user interface 18 may be separate devices, in certain embodiments, the processor 16 and the user interface 18 may be provided as a single unit.

Returning now to processing of the data received, the processor 16 may use an iterative approach to arrive at a determined position and orientation of the at least one EM sensor 12, array of EM sensors 14, or another tracked object. For example, an initial "seed" approximation of position and orientation may be provided, or resolved by initial measurements of the system 10 and the processor 16. The processor 16 may then use this approximate position and orientation in subsequent algorithms to predict the magnetic field characteristics, and determine a new estimate of position. The processor 16 may then compare the measured and calculated values, and consider the need to calculate new estimates of the magnetic field characteristics. The iteration of estimating and comparing may continue until the estimated values are sufficiently similar to the position and orientation actually sensed.

Accordingly, it is desirable that the system 10 be configured to ensure that a determination of position and orientation be done efficiently and accurately. For example, to increase the accuracy of the measured values of the electromagnetic fields and, thus, the seed approximation, the array of EM sensors 14 may be oriented in a given arrangement. One arrangement may include an array of EM sensors 14 located in a single plane about a region in a quadrilateral configuration (e.g., four sensors located on the corners of a table). In many instances, this configuration may provide sufficient accuracy to determine position and orientation of at least one EM sensor 12 relative to the array of EM sensors 14. For example, in medical tracking systems where a device is tracked in a patient on a table it is known that the at least one EM sensor 12 is above the plane containing the array of EM sensors 14 and, thus, it is known that z is positive and processing must only resolve the x and y position and the z distance. However, if it is unknown whether the at least one EM sensor 12 is located above or below the plane containing the array of EM sensors 14, processing must also resolve the z direction. A configuration of an array of EM sensors located in one plane may make this impossible. For example, the same mutual inductance measurements may be present for at least one EM sensor 12 located above the plane at a given position (x, y, z) and at least one EM sensor 12 located below the plane at a given position. In both locations ((x, y, z) and (x, y, −z)) the at least one EM sensor 12 is the same distance from each of the respective array of EM sensors 14. Thus, the mutual inductance measurements and their ratios used in processing are the same. Therefore, processing is unable to resolve on which side of the plane the at least one EM sensor 12 (e.g., the tracked device) is located.

In light of the above considerations and concerns, a system is needed that can accurately track the position of an object in all three dimensions. Provided is a system that includes an EM coil arrangement that provides for tracking of an object in three dimensions (i.e., x, y and z dimensions) including the relative location along the z axis.

Turning now to FIG. 2, an EM coil arrangement 20 is depicted in accordance with an exemplary embodiment of the present technique. In an embodiment, a plurality of EM sensors 14 may be arranged at the vertices of a volumetric region 22. The array of EM sensors 14 may be arranged with at least one of the EM sensors 14 not located in the same plane as the other sensors. For example, as depicted in FIG. 2, an array of four EM sensors 14 may be located at the vertices of a tetrahedron. The four EM sensors 14 are spaced apart from each other, and are not all in the same plane. As will be appreciated, a tetrahedron is a polyhedron composed of four triangular faces, three of which meet at each vertex. As will also be appreciated, three points in space may form a plane. Thus, as depicted in FIG. 2, the EM coil arrangement 20 includes three of the EM sensors 14 located in a single plane (coplanar) with a fourth of the EM sensors 14 that is not contained in the same plane.

As will be appreciated by those of ordinary skill in the art, the shape of the tetrahedron may take several forms. In an embodiment the tetrahedron may include a "regular" tetrahedron. For example, FIG. 2 illustrates the array of EM sensors 14 disposed at the vertices of a regular tetrahedron. Further, an embodiment consistent with FIG. 2 may include four EM sensors 14 spaced equally at a distance of about 4 cm to about 6 cm to form the vertices of a regular tetrahedron. As will be appreciated by those ordinarily skilled in the art, in a "regular" tetrahedron configuration, the four EM sensors 14 may be located an equal distance apart and, therefore, the array of EM sensors may be configured at any given distance that meets the requirements of the application.

Figure 3:
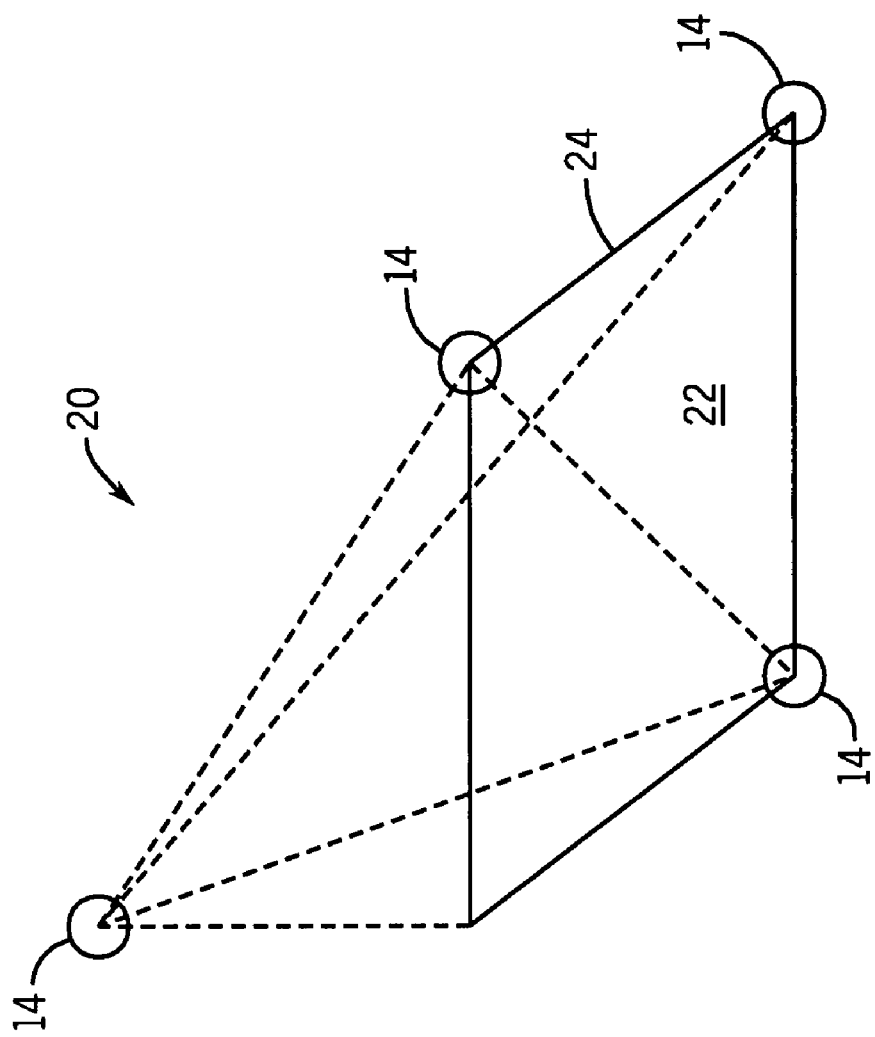
FIG. 3 is an illustration of an alternate exemplary sensor arrangement in accordance with certain aspects of the present technique.

In another embodiment, the tetrahedron may not be "regular." In other words, the array of four EM sensors 14 may not be coplanar and may be spaced at unequal distances. For example, as depicted in FIG. 3, the base of the tetrahedron may be defined by three of the EM sensors 14 located at three corners of a planar region 24 with a fourth of the EM sensors 14 located above a fourth corner of the region 24. As will be appreciated by those ordinarily skilled in the art, the vertices of the tetrahedron may be located at any four points in space that are not coplanar.

To form the array of EM sensors 14 that are disposed at the vertices of the tetrahedron, various EM sensor configurations may be used. For example, the EM sensor may include a single coil or multiple coils. In an embodiment, each of the EM sensors 14 may include a coil trio (described previously). Thus, the array of four EM sensors 14 may include a total of 12 coils. For example, the EM coil arrangement 20 may include four one-centimeter-cube coil trios (e.g., three sets of coils wound about a one-centimeter-cubical bobbin) that are equally spaced, about 4 cm to about 6 cm apart. In these configurations, the coil trios and their spatial relationship may be precisely characterized to assist in processing. For example, prior to using the coil arrangement 20 to receive magnetic fields each coil and their combination may be calibrated.

In another embodiment, the array of EM sensors 14 may employ other types of magnetic field sensors. For example, the array of EM sensors 14 may include Hall Effect, magnetoresistance and flux gate devices. As will be appreciated by those of ordinary skill in the art, the array of EM sensors 14 may include any suitable device which is capable of providing a signal indicative of the magnetic field (e.g., mutual inductance) to the processor 16 for processing.

As for the configuration of the at least one EM sensor 12, it should be noted that application itself may dictate the EM sensor type. For example, in medical applications it is often desired that that an EM sensor be inserted into a patient. Therefore, objects that are to be tracked may employ a single dipole coil EM sensor with a small profile as opposed to a multi-coil EM sensor with a relatively large profile. A single coil EM sensor acting as an EM field generator or transmitter needs no characterization and easily fits inside the tip of an instrument or device. As will be appreciated, this limitation may be driven by the specific application and is not absolute. For example, in an application where the device to be tracked may accommodate a larger EM sensor, a coil trio or other sensor may be used.

To provide for tracking of a medical instrument or device, the at least one EM sensor 12 or the array of EM sensors 14 may be coupled to an instrument 26. In medical tracking applications an object to be tracked may include an instrument or device 26 used during a medical procedure. For example, at least one EM sensor 12 may be coupled to an instrument or device 26 inserted into the body of a patient 28 and tracked by the array of EM sensors 14 (see FIG. 4). As will be appreciated by those ordinarily skilled in the art, the present technique may be used to track a variety of instruments and devices 26 used during medical procedures. For example, the instrument or device 26 may include a drill, a guide wire, an endoscope, a laparoscope, a biopsy needle, an ablation device or other similar devices.

Implementations in accordance with the present technique may take a variety of forms. In an embodiment, the EM coil arrangement 20 may be positioned proximate to a patient 28 and a tracked instrument or device 26. For example, as depicted in FIG. 4, the EM coil arrangement 20 may be contained in a rigid support 30 that is securely fixed about the head and nose of a patient 28. Thus, the EM coil arrangement 20 may allow for sensing of the electromagnetic field (e.g., mutual inductance) between the array of EM sensors 14 and at least one EM sensor 12 attached to an instrument or device 26 that is proximal or internal to the patient 28. For example, in a medical application it may be necessary to remotely insert an instrument or device 26 to perform procedures internal to the patient 28 and out of the line of sight of the operating physician. As will be appreciated by those of ordinary skill in the art, this technique may be accommodated for use in a variety of applications for tracking.

Figure 5:
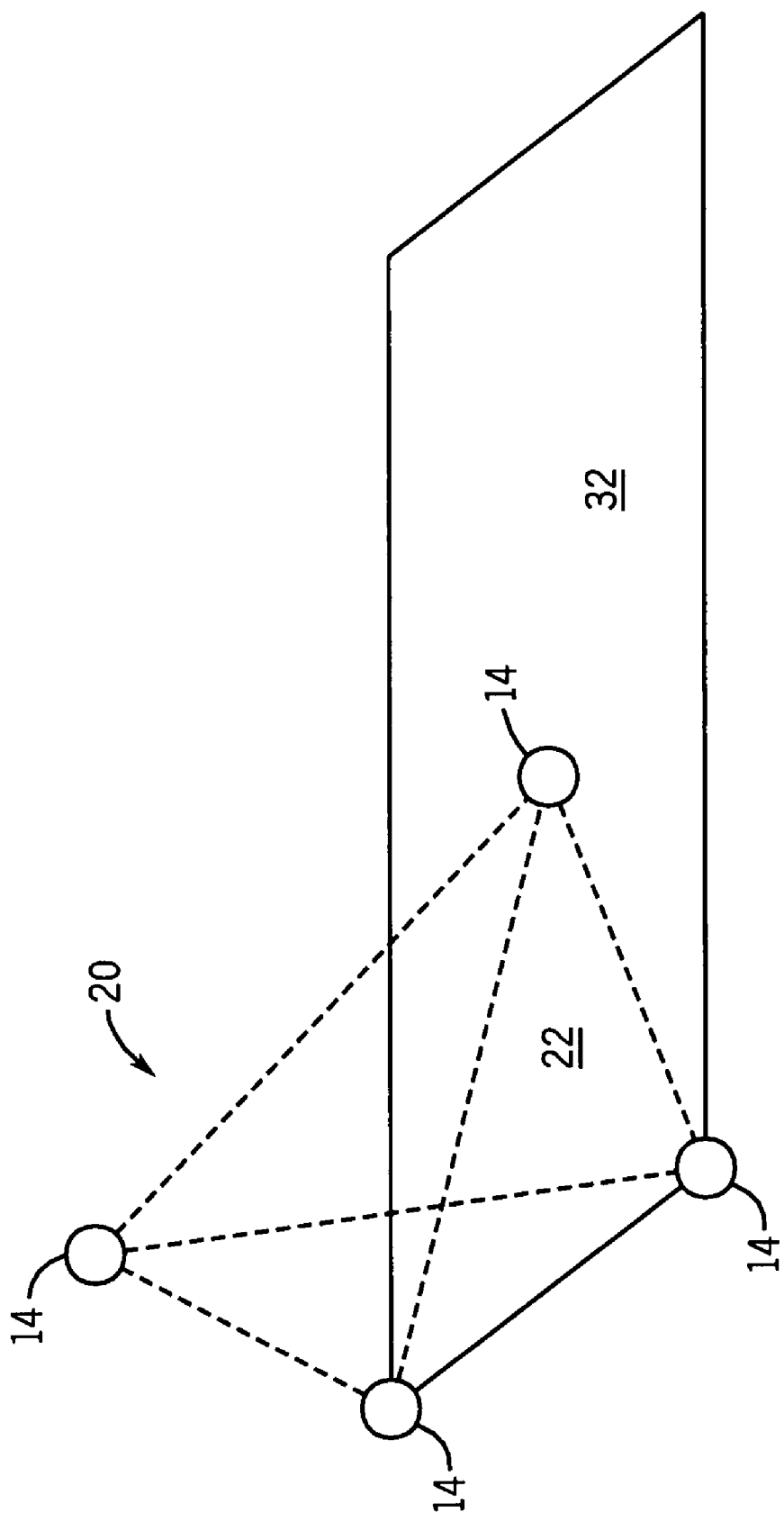
FIG. 5 is an illustration of the exemplary sensor arrangement of FIG. 2 disposed about a table in accordance with aspects of the present technique.

Using a similar EM coil arrangement 20, another implementation of the present technique may include affixing the array of EM sensors 14 to a surface. In an embodiment, the surface may include a surgical table 32. For example, as depicted in FIG. 5, three EM sensors 14 may be disposed on the surface of the table 32 with a fourth EM sensor 14 located above the surface (i.e., not coplanar). In this configuration, the EM coil arrangement 20 may prove beneficial to provide more accurate tracking in the "z" direction as well as provide processing with a means to resolve the location of an instrument above or below the surface of the table 32. As will be appreciated by those of ordinary skill in the art, the EM coil arrangement 20 may include affixing the EM sensors 14 in any suitable non-coplanar form. For example, three EM sensors 14 may be located in the plane of the table 32 with a fourth EM sensor 14 located below the surface of the table 32.

Figure 6:
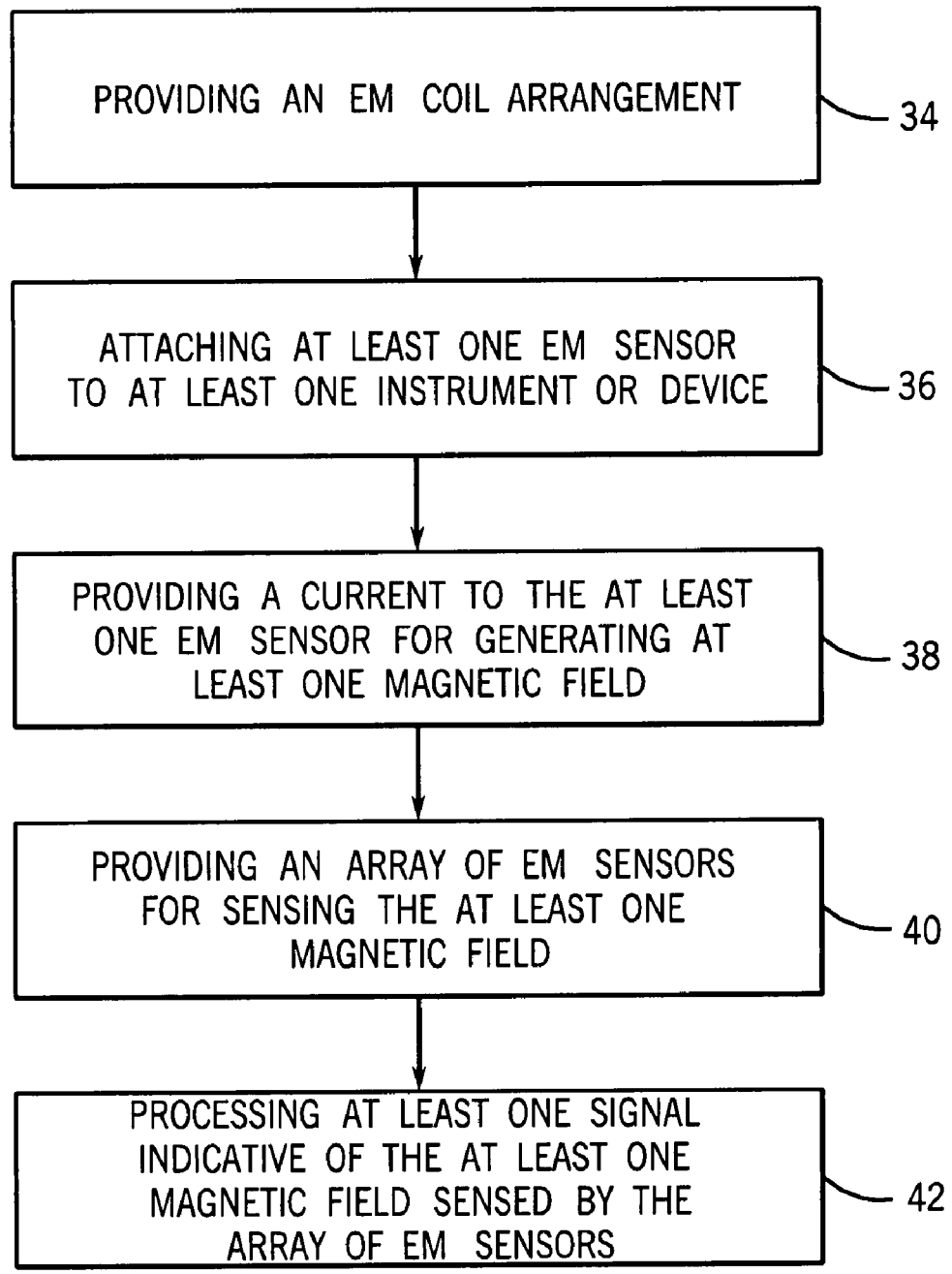
FIG. 6 is a flowchart depicting a method of processing in accordance with aspects of the present technique.

A method of using the tracking system 10 is depicted in flowchart form in FIG. 6. As described above, the tracking system 10 may include at least one EM sensor 12 and an EM coil arrangement 20. In an embodiment, the at least one EM sensor 12 may include a single dipole coil affixed to an instrument or device 26, and the EM coil arrangement 20 may include an array of EM sensors 14 positioned at the vertices of a volumetric region 22. In such an embodiment, the EM coil arrangement 20 may be affixed proximate to a desired tracking region. Similarly, the at least one EM sensor 12 may be positioned in a tracking area proximate to the EM coil arrangement 20 to provide for tracking of the instrument or device 26. Accordingly, FIG. 6 depicts the step of providing an EM coil arrangement 20 at block 34 and attaching at least one EM sensor 12 to at least one instrument or device 26 at block 36. In an embodiment, the at least one EM sensor 12 may include a single dipole coil affixed to an instrument or device 26 and the EM coil arrangement 20 may include four EM sensors 14 positioned at the vertices of a volumetric region 22, such as a tetrahedron. As discussed previously, providing the array of EM sensors 14 may include providing a coil, coil trio, Hall Effect, magnetoresistance, flux gate device or any suitable device which is capable of providing a signal indicative of the magnetic field (e.g., mutual inductance) to the processor 16 for processing. It should be noted that positioning the at least one EM sensor 12 may include providing a stationary EM sensor 12, used as a dynamic reference for the tracking system, as well as a moving EM sensor 12, attached to an instrument or device 26, as the system is configured to track both.

As depicted at block 38, of FIG. 6, the method further includes providing a current to the at least one EM sensor 12 for generating at least one magnetic field. Embodiments of the method include the at least one EM sensor 12 having a current driven across a coil to generate at least one magnetic field of a given magnitude, phase and frequency. For example, as described previously, the at least one EM sensor 12 may include a single dipole coil that is provided a drive current via the processor 16 and generates a corresponding magnetic field that may be sensed by the array of EM sensors 14.

Accordingly, block 40 of FIG. 6 includes a complementary step of providing an array of EM sensors 14 for sensing the at least one magnetic field. For example, an embodiment may include each coil of the array of EM sensors 14 of the EM coil arrangement 20 sensing a magnetic field indicative of the mutual inductance across each coil and transmitting that signal to the processor 16. Thus, in an embodiment, the processor 16 may receive twelve signals indicative of the mutual inductance across each of the coils, for example, where the each of the array of EM sensors 14 comprises a coil trio.

As will be appreciated by those of ordinary skill in the art, the discussion of providing an EM coil arrangement at block 34, attaching at least one EM sensor to at least one instrument or device at block 36, providing a current to the at least one EM sensor for generating at least one magnetic field at block 38, and providing an array of EM sensors for sensing the at least one magnetic field at block 40 may be accomplished in a variety of suitable orders. Further, as will be appreciated by those of ordinary skill in the art, due to reciprocity, the steps of generating a magnetic field at block 38 and sensing a magnetic field at block 40 are not limited to the embodiments described. For example, an embodiment may include the array of EM sensors 14 configured to generate at least one magnetic field and the at least one EM sensor 12 configured to sense the at least one magnetic field.

As will be appreciated, processing the signal indicative of the magnetic field may be performed to resolve a desired parameter. For example, the embodiment of the method in FIG. 6 may include processing at least one signal indicative of the at least one magnetic field sensed by the array of EM sensors to determine a position and/or orientation of the at least one instrument or device 26, as depicted at block 42. Processing may include the processor 16 receiving data, including a signal indicative of the magnetic field sensed (e.g., mutual inductance), and performing several functions to arrive at a resolved position and/or orientation. In an EM tracking system 10, processing may take several different forms including dependence on prior recorded data or analytical solutions, or a combination of the two.

In an embodiment, processing may include dependence on data that was previously recorded. For example, a suitable method may include the use of a Look-Up-Table (LUT) that may be derived by measuring the magnetic field characteristics at every point of interest in the tracking volume. In this form of processing, the measured values of the magnetic field may be transmitted from the array of EM sensors 14 to the processor 16, and the processor 16 may then search a database of pre-stored data sets of similar measurements. Processing may then match up the current measurements to a similar pre-stored data set associated with a given position and/or orientation. Thus, the processor 16 may use the position and orientation data in subsequent processing or output the data to a user interface 18. As will be appreciated this technique may require a sizable amount of memory and processing power, and therefore may not be suitable in all systems.

Other forms of processing may include analytical approaches. In an embodiment, processing may include triangulating a position based on the ratios of mutual inductance sensed between the coil of the at least one EM sensor 12 and the coils of the array of EM sensors 14. For example, a suitable equation representative of mutual inductance may include:

$$L = \frac{\mu_0 \times A_{effc} \times A_{effe}}{R^3} \times C_1 \qquad (1)$$

Wherein:
L=mutual inductance magnitude in henries;
L=the permeability of free space=$\Pi*4\times10^{-7}$ henries/meter;

R=distance between sensors;
$A_{effc}$=effective area of a single dipole coil;
$A_{effe}$=effective area of a coil trio; and
$C_1$=a factor between 1 and 2 that may be determined based upon the orientation of the generating sensor.
Wherein $C_1$ is equal to the square root of two, solving equation 1 for the distance R gives:

$$R = \sqrt[3]{\frac{\mu_o \times A_{effc} \times A_{effe} \times \sqrt{2}}{L}} \quad (2)$$

Using equation 2 and the mutual-inductance sensed from each respective EM sensor 14, the distances between each coil of the EM sensor 14 and the coil of the at least one EM sensor 12 may be determined. By triangulation of the distances, a relative position and orientation of the at least one EM sensor 12 may be determined.

As will be appreciated by those ordinarily skilled in the art, any suitable algorithm or method of processing may be used to relate the signals sensed by the EM sensors to a position and/or orientation. For example, an alternate method of processing may include a consideration of the magnetic field gradient. In the exemplary embodiment described above, each of the coils of the array of EM sensors 14 may transmit a signal to the processor 16 that is indicative of the mutual inductance at each respective coil. The processor 16 may then use these mutual inductance measurements to resolve and average mutual inductance that is representative of the mutual inductance at a point central to the tetrahedron. Processing may then use the mutual inductance calculated at each of the EM sensors 14 and the averaged "central point" to determine the gradient of the magnetic field at the "central point." With the gradient of the central point estimated, any suitable algorithm may be used to determine the position vector between the central point and the at least one EM sensor 12. For example, where the magnetic flux density generated at r is expressed as:

$$B = \frac{\mu_o}{4\pi} \frac{3(p \cdot n)n - p}{r^3} \quad (3)$$

Where:
$\mu_o$=the permeability of free space=$\Pi * 4 \times 10^{-7}$ henries/meter;
r=distance between sensors;
p=the magnetic moment; and
n=the unit vector of (|r|/r).
And the variance of the magnetic field at two points is represented by:

$$B - B' = -\frac{3}{r} B dr \quad (4)$$

And the gradient of the magnetic field may be represented as:

$$B - B' = \begin{pmatrix} \partial_x B_x & \partial_y B_x & \partial_z B_x \\ \partial_x B_y & \partial_y B_y & \partial_z B_y \\ \partial_x B_z & \partial_y B_z & \partial_z B_z \end{pmatrix} ndr \quad (5)$$

Then the position vector (r) from the at least one EM sensor to the central point of the tetrahedron may be represented as:

$$r = -3 \begin{pmatrix} \partial_x B_x & \partial_y B_x & \partial_z B_x \\ \partial_x B_y & \partial_y B_y & \partial_z B_y \\ \partial_x B_z & \partial_y B_z & \partial_z B_z \end{pmatrix}^{-1} \begin{pmatrix} B_x \\ B_y \\ B_z \end{pmatrix} \quad (6)$$

Thus, the processing may resolve the position of the at least one EM sensor 12 relative to the position of the array of EM sensors 14 in the EM coil arrangement 20. As will be appreciated by those of ordinary skill in the art, any suitable method of processing may be implemented to resolve the approximate position.

As described previously, the processor 16 may implement the above technique to determine an approximate position for the at least one EM sensor 12 that is being tracked by the system 10. This initial position estimate (commonly referred to as a "seed guess") may be used as the determined position or used in subsequent algorithms to more accurately determine the position and/or orientation of the at least one EM sensor 12. For example, after the "seed guess" is determined, a suitable "Goodness-of-fit" calculation may be performed to determine if the position and/or orientation are within an acceptable range. The Goodness-of-fit ($G_f$) may include a dimensionless measure of the discrepancies between the modeled mutual inductance $L_{model}$ (which are functions of position estimates $R_{model}$ and orientation estimate $O_{model}$), and the measured mutual inductance $L_{meas}$ (for one transmitter coil and twelve receiver coils):

$$G_f = \frac{\sum_{r=1}^{12} (L_{model} - L_{meas})_r^2}{\sum_{r=1}^{12} (L_{meas})_r^2} \quad (7)$$

When $G_f$ is small, the remaining errors may be small, and thus the errors in R model and $O_{model}$ are small. If $G_f$ is high, then the approximate characteristics of the system are not correct. Thus, the "good fits" may indicate that processing has output an acceptably accurate position and/or orientation which may be output to the user interface 18 or used in subsequent processing.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:
1. A tracking system, comprising:
an array of electromagnetic receivers that sense at least one characteristic of a magnetic field, the array of electromagnetic sensors comprising three co-planar electromagnetic sensors and a fourth electromagnetic sensor that is not co-planar with the three co-planar sensors, wherein the three co-planar electromagnetic sensors and the fourth electromagnetic sensor are each located at a vertex of a tetrahedron, and the three co-planar electromagnetic sensors and the fourth electromagnetic sensor each comprise industry-standard coil architecture (ISCA) type coils; and a processor that receives a signal indicative of the at least one characteristic from the array of electromagnetic receivers and processes the signal to resolve a position of an electromagnetic field generator that generated the magnetic field relative to the array of electromagnetic receivers, wherein processing the at least one signal comprises determining an average magnetic field gradient at the center of the array of electromagnetic receivers, and wherein the average magnetic field gradient is processed to resolve the position of the electromagnetic field generator relative to the array of electromagnetic receivers.

2. The electromagnetic coil arrangement of claim 1, wherein the three co-planar electromagnetic sensors and the fourth electromagnetic sensor are located an equal distance apart.

3. The electromagnetic coil arrangement of claim 1, wherein the three co-planar electromagnetic sensors and the fourth electromagnetic sensor are not all an equal distance apart.

4. The tracking system of claim 1, wherein the signal indicative of the at least one characteristic of the magnetic field is indicative of the mutual inductance at each respective elemctromagnetic reciever.

5. The tracking system of claim 4, wherein processing the at least one signal comprises determining an average mutual inductance that is representative of the mutual inductance at a point central to the tetrahedron, wherein the average mutual inductance so determined is used in determining the average magnetic field gradient at the center of the array of electromagnetic receivers.

6. A method of electromagnetic tracking comprising:
providing at least one electromagnetic field generator for generating at least one magnetic field;
providing an array of electromagnetic receivers for sensing at least one characteristic of the at least one magnetic field, wherein the array of electromagnetic receivers comprises three co-planar electromagnetic receivers and a fourth electromagnetic receiver that is not co-planar with the three co-planar receivers, and wherein the three co-planar electromagnetic receivers and the fourth electromagnetic receiver are each located at a vertex of a tetrahedron;
transmitting at least one signal indicative of the at least one characteristic of the at least one magnetic field to a processor; and
processing the at least one signal to resolve a position of the at least one electromagnetic field generator that generated the at least one magnetic field relative to the array of electromagnetic receivers, wherein processing the at least one signal comprises determining an average magnetic field gradient at the center of the array of electromagnetic receivers, and wherein the average magnetic field gradient is processed to resolve the position of the electromagnetic field generator relative to the array of electromagnetic receivers.

7. The method of claim 6, wherein the array of electromagnetic receivers is coupled to a rigid support frame.

8. The method of claim 6, wherein the array of electromagnetic receivers is coupled to a table configured for use in surgery.

9. The method of claim 6, wherein the at least one signal indicative of the at least one characteristic of the at least one magnetic field is indicative of the mutual inductance at each respective elemctromagnetic reciever.

10. The method of claim 9, wherein processing the at least one signal comprises determining an average mutual inductance that is representative of the mutual inductance at a point central to the tetrahedron, wherein the average mutual inductance so determined is used in determining the average magnetic field gradient at the center of the array of electromagnetic receivers.

* * * * *